United States Patent
Saimi et al.

(10) Patent No.: US 8,389,598 B2
(45) Date of Patent: Mar. 5, 2013

(54) DENTAL POLYMERIZABLE COMPOSITION AND KIT THEREFOR

(75) Inventors: Yasukazu Saimi, Moriyama (JP);
Yasuhiro Nukii, Moriyama (JP);
Masami Arata, Moriyama (JP)

(73) Assignee: Sun Medical Co., Ltd., Moriyama-Shi (JP)

( * ) Notice: Subject to any disclaimer, the term of this patent is extended or adjusted under 35 U.S.C. 154(b) by 314 days.

(21) Appl. No.: 12/678,068

(22) PCT Filed: Sep. 12, 2008

(86) PCT No.: PCT/JP2008/066940
§ 371 (c)(1),
(2), (4) Date: Jun. 11, 2010

(87) PCT Pub. No.: WO2009/035165
PCT Pub. Date: Mar. 19, 2009

(65) Prior Publication Data
US 2011/0028589 A1 Feb. 3, 2011

(30) Foreign Application Priority Data
Sep. 13, 2007 (JP) ................. 2007-238177

(51) Int. Cl.
*A61L 24/06* (2006.01)
*A61K 6/083* (2006.01)
*A61C 5/09* (2006.01)
*C08L 33/12* (2006.01)
*C08L 33/10* (2006.01)
*C08F 265/04* (2006.01)
*C08F 265/06* (2006.01)
*C08F 120/18* (2006.01)

(52) U.S. Cl. ...... 523/115; 523/113; 523/200; 433/228.1; 106/35; 525/55; 525/227; 525/228; 525/242; 525/244; 526/329.7

(58) Field of Classification Search .................. 523/115, 523/113, 200; 433/228.1; 106/35; 525/55, 525/227, 228, 242, 244; 526/329.7
See application file for complete search history.

(56) References Cited

U.S. PATENT DOCUMENTS

| 4,648,843 | A | 3/1987 | Mitra |
| 4,820,744 | A | 4/1989 | Kubota et al. |
| 4,873,269 | A | 10/1989 | Nakazato |
| 5,043,361 | A | 8/1991 | Kubota et al. |
| 5,276,070 | A * | 1/1994 | Arroyo .................... 523/117 |
| 5,407,973 | A | 4/1995 | Hasegawa et al. |
| 2007/0032567 | A1 * | 2/2007 | Beyar et al. .................... 523/116 |
| 2010/0168271 | A1 * | 7/2010 | Beyar et al. .................... 523/116 |

FOREIGN PATENT DOCUMENTS

| JP | 57-203006 A | 12/1982 |
| JP | 61-241303 A | 10/1986 |
| JP | 62-246514 A | 10/1987 |
| JP | 63-35508 A | 2/1988 |
| JP | 2-212407 A | 8/1990 |
| JP | 5-78531 A | 3/1993 |
| JP | 5-78531 B2 | 10/1993 |
| JP | 6-219919 A | 8/1994 |
| JP | 7-80736 B2 | 8/1995 |
| JP | 2008-174461 A | 7/2008 |

OTHER PUBLICATIONS

International Search Report, dated Nov. 4, 2008, issued in corresponding PCT/JP2008/066940.

* cited by examiner

*Primary Examiner* — Michael Pepitone
(74) *Attorney, Agent, or Firm* — Birch, Stewart, Kolasch & Birch, LLP

(57) ABSTRACT

The present invention provides a dental polymerizable composition which has excellent handling property by the brush-dip technique and the bulk-mix technique, particularly excellent handling property by the brush-dip technique, contains few air bubbles, is excellent in color tone, polishability, mechanical properties and the discoloration resistance of a cured product at the time of curing and is used for many purposes such as the repair of a denture base or artificial tooth, a tooth crown prosthetic restoration and a temporary prosthetic restoration which is used until a bridge is completed when it is a two-composition type self-curing resin. The dental polymerizable composition comprises three different types of (meth)acrylate polymer particles, each having specific particle size characteristics and specific molecular weight characteristics.

22 Claims, No Drawings

DENTAL POLYMERIZABLE COMPOSITION AND KIT THEREFOR

CROSS-REFERENCE TO RELATED APPLICATIONS

This application is a National Stage Application of PCT/2008/066940, filed Sep. 12, 2008. This application also claims priority under 35 USC 119(a) to Japanese patent application no. 2007-238177, filed in Japan on Sep. 13, 2007. The entire contents of all of the above are herein incorporated by reference.

TECHNICAL FIELD

The present invention relates to a dental polymerization composition. More specifically, it relates to a dental polymerizable composition which has excellent handling property by the brush-dip technique and the bulk-mix technique, particularly excellent handling property for building up with resin by the brush-dip technique, that is, slurry hardly falls, spreads well and releases from a brush easily, contains few air bubbles, is excellent in color tone, polishability, mechanical properties and discoloration resistance and is used for many purposes such as the repair of a denture base or artificial tooth, a tooth crown prosthetic restoration, a temporary prosthetic restoration which is used until a bridge is completed, or the restoration of a tooth germ when it is a multi-composition type polymerizable at normal temperature.

BACKGROUND ART

A powder-liquid mixture quick-cure resin comprising (meth)acrylate polymer powders and a (meth)acrylate monomer is frequently used for the repair of a denture base, the manufacture of a temporary crown, the repair of an artificial tooth and the restoration of a tooth germ. In recent years, due to a growing number of clinical cases in which a final prosthetic restoration is attached after the restoration of the gum is awaited for a long time, as exemplified by an implant treatment, a temporary crown which is stable in color tone, mechanical strength and discoloration resistance for a long time has been desired, and various products are now available on the market. To make this temporary crown aesthetically excellent, mainly the brush-dip technique in which a brush for dental technicians is wetted with a (meth)acrylate containing a reducing agent and (meth)acrylate polymer powders containing a radical generator are adhered to the brush for application is frequently employed. When the crown is manufactured by the brush-dip technique and slurry collected into the brush falls easily, it is difficult to build up the slurry, thereby making it difficult to produce a fine crown form. When the slurry does not fall, the polymer powders cannot be spread thin with the brush and there occurs a problem with build-up on a margin. When attention is paid to a polymerization initiator, since an organic peroxide and a tertiary aromatic cyclic amine are used, the crown yellows upon curing, thereby deteriorating its aesthetics, and a cured product yellows or colors in the oral cavity, thereby impairing its aesthetics in an early stage. To solve this problem, there is proposed a method in which a powder material containing a pyrimidinetrione derivative and an organic metal compound and a liquid material containing an organic halogen compound and an aromatic cyclic tertiary amine are used to improve brush handling property, the inclusion of air bubbles and aesthetics (refer to JP-A 6-219919). There is also proposed a method in which a specific triazole-based compound is added to prevent discoloration at the time of curing (refer to JP-B 5-78531).

DISCLOSURE OF THE INVENTION

It is an object of the present invention to provide a dental polymerizable composition.

It is another object of the present invention to provide a dental polymerizable composition which has excellent handling property by the brush-dip technique and the bulk-mix technique, particularly excellent handling property for building up with resin by the brush-dip technique, that is, slurry hardly falls, spreads well and releases from a brush easily, contains few air bubbles, is excellent in color tone, polishability, mechanical properties and discoloration resistance and is used for many purposes such as the repair of a denture base or artificial tooth, a tooth crown prosthetic restoration, a temporary prosthetic restoration which is used until a bridge is completed, or the restoration of a tooth germ when it is a two- or three-composition type, especially powder-liquid type resin polymerizable at normal temperature.

Other objects and advantages of the present invention will become apparent from the following description.

According to the present invention, the above objects and advantages of the present invention are attained by a dental polymerizable composition comprising a polymerizable monomer (a), a radical generator (b) and (meth)acrylate polymer particles (def), wherein the (meth)acrylate polymer particles (def) contain powders (d) having a particle size distribution of 65 to 400 μm, a median diameter of 70 to 120 μm and a molecular weight ($M_G$) in terms of PMMA measured by GPC of 500,000 to 1,150,000, powders (e) having a particle size distribution of 65 to 400 μm, a median diameter of 70 to 120 μm and a molecular weight ($M_G$) in terms of PMMA measured by GPC of more than 1,150,000 and 2,000,000 or less, and powders (f) having a particle size distribution of 10 to 65 μm, a median diameter of 20 to 60 μm and a molecular weight ($M_G$) in terms of PMMA measured by GPC of 300,000 to 3,000,000 as the main components, at least the polymerizable monomer (a) and the radical generator (b) are contained in different compositions I and III, respectively, and a mixture of these compositions is curable.

The dental polymerizable composition is preferably a two-composition type dental polymerizable composition wherein the composition I comprises at least the polymerizable monomer (a) and a reducing agent (c) capable of decomposing the radical generator (b), the composition III comprises at least the radical generator (b) and (meth)acrylate polymer particles having a particle size distribution that at least one particle diameter peak is existent at a range of 55 to 150 μm (more than 55 μm and 150 μm or less) and also at a range of 20 to 55 μm and at least three number average molecular weight (Mn) peaks Pd, Pe and Pf at a range of 50,000 to 200,000 (not including 200,000), a range of 350,000 to 500,000 (not including 350,000) and a range of 200,000 to 350,000, respectively, and a mixture of the composition I and the composition III is curable.

Further, the dental polymerizable composition is preferably characterized in that the content of powders having a particle diameter of 65 to 400 μm is 99 to 70 wt %, and the content of powders having a particle diameter of 1 to 30 μm is 1 to 30 wt %, and the content of powders having a number average molecular weight (Mn) of 50,000 to 200,000 (not including 200,000) is 20 to 75 wt %, the content of powders having a number average molecular weight (Mn) of 400,000 to 550,000 is 20 to 75 wt %, and the content of powders having a number average molecular weight (Mn) of 200,000 to 400,000 is 1 to 30 wt % based on 100 wt % of the total of the (meth)acrylate polymer particles.

BEST MODE FOR CARRYING OUT THE INVENTION

In the present invention, "(meth)acryl-" in the names of compounds and the names of functional groups means "acryl- and/or methacryl-", and "XX to YY" (XX and YY are numerical values) in preferred numerical ranges means "XX or more and/or YY or less" unless stated otherwise.

A description is first given of the forms of the composition I and the composition III (or II). Since the composition I contains a polymerizable monomer, it is in liquid form in most cases. It may be in paste form. Meanwhile, since the composition III contains (meth)acrylate-based polymer particles and a radical generator having not so high stability in most cases, it is preferably in solid form such as powder. Therefore, the composition I in liquid form and the composition III in powdery form will be mainly explained in the following description but the present invention is not limited to these forms. The present invention is a dental polymerizable composition which is a mixture of the compositions I and III able to be cured by redox polymerization or the like as required. When the radical generator is in liquid form, it is preferred, for example, that the (meth)acrylate polymer particles (def) should be prepared as a composition II separate from the compositions I and III and that the radical generator of the composition III should be added to the composition I and mixed with the composition II.

A description is subsequently given of the polymerizable monomer (a) contained in the composition I. A known polymerizable compound may be used as the polymerizable monomer (a), as exemplified by (i) a monofunctional polymerizable monomer, (ii) a bifunctional polymerizable monomer, (iii) a trifunctional polymerizable monomer and (iv) a tetra or more-functional polymerizable monomer. Out of these, a (meth)acrylate compound is particularly preferred. Examples of these monomers are given below. As a matter of course, two or more compounds may be used in combination.

(i) Monofunctional Polymerizable Monomer

Examples of the monofunctional polymerizable monomer include (meth)acrylate-based polymerizable monomers such as methyl(meth)acrylate, ethyl(meth)acrylate, n-butyl(meth)acrylate, isopropyl(meth)acrylate, 2-ethylhexyl(meth)acrylate, n-lauryl(meth)acrylate, n-stearyl(meth)acrylate, behenyl(meth)acrylate, 2-hydroxyethyl(meth)acrylate, 2-hydroxy-3-phenoxypropyl(meth)acrylate, tetrahydrofurfuryl(meth)acrylate, glycidyl(meth)acrylate, methoxyethylene glycol(meth)acrylate, methoxydiethylene glycol(meth)acrylate, methoxytriethylene glycol(meth)acrylate, methoxypolyethylene glycol(meth)acrylate, ethoxyethylene glycol(meth)acrylate, ethoxydiethylene glycol(meth)acrylate, ethoxytriethylene glycol(meth)acrylate, ethoxypolyethylene glycol(meth)acrylate, phenoxyethylene glycol(meth)acrylate, phenoxydiethylene glycol(meth)acrylate, phenoxytriethylene glycol(meth)acrylate, phenoxypolyethylene glycol(meth)acrylate, cyclohexyl(meth)acrylate, benzyl(meth)acrylate, 3-chloro-2-hydroxypropyl(meth)acrylate, isobornyl(meth)acrylate, dicyclopentanyl(meth)acrylate, dicyclopentenyl(meth)acrylate, dicyclopentenyloxyethyl(meth)acrylate, N-(meth)acryloyl morpholine, trifluoroethyl(meth)acrylate and perfluorooctyl (meth)acrylate.

Known acid group-containing monofunctional polymerizable monomers may also be used. The compounds include phosphoric acid group-containing polymerizable monomers, pyrophosphoric acid group-containing polymerizable monomers, thiophosphoric acid group-containing polymerizable monomers, carboxylic acid group-containing polymerizable monomers and sulfonic acid group-containing polymerizable monomers. The content of the acid group-containing polymerizable monomer is not more than 20 wt %, preferably not more than 10 wt %, more preferably not more than 5 wt % of the polymerizable monomer (a). When the content of the acid group-containing polymerizable monomer is higher than 20 wt %, the water resistance of the cured product and the storage stability of the composition I may be deteriorated by the acid group disadvantageously.

As examples of the acid group-containing polymerizable monomer, the phosphoric acid group-containing polymerizable monomers include 2-(meth)acryloyloxyethyl dihydrogen phosphate, 3-(meth)acryloyloxypropyl dihydrogen phosphate, 10-(meth)acryloyloxydecyl dihydrogen phosphate, 12-(meth)acryloyloxydodecyl dihydrogen phosphate, (meth)acryloyloxyethylphenyl phosphate and (8-(meth)acryloyloxy)octyl-3-phosphonopropionate.

The pyrophosphoric acid group-containing polymerizable monomers include di[2-(meth)acryloyloxyethyl]pyrophosphate, di[4-(meth)acryloyloxybutyl]pyrophosphate, di[8-(meth)acryloyloxyoctyl]pyrophosphate and di[12-(meth)acryloyloxydodecyl]pyrophosphate.

The thiophosphoric acid group-containing polymerizable monomers include 2-(meth)acryloyloxyethyl dihydrogen thiophosphate, 3-(meth)acryloyloxypropyl dihydrogen thiophosphate, 10-(meth)acryloyloxydecyl dihydrogen thiophosphate and 12-(meth)acryloyloxydodecyl dihydrogen thiophosphate.

The carboxylic acid group-containing polymerizable monomers include (meth)acrylic acid, 4-(meth)acryloyloxyethyloxycarbonyl phthalic acid, 4-(meth)acryloyloxybutyloxycarbonyl phthalic acid, 4-(meth)acryloyloxyoctyloxycarbonyl phthalic acid, 4-(meth)acryloyloxydecyloxycarbonyl phthalic acid and acid anhydrides thereof, 6-(meth)acryloylaminohexylcarboxylic acid, 8-(meth)acryloylaminooctylcarboxylic acid and 11-(meth)acryloyloxy-1,1-undecanedicarboxylic acid.

The sulfonic acid group-containing polymerizable monomers include 2-(meth)acrylamidoethylsulfonic acid, 3-(meth)acrylamidopropylsulfonic acid, 4-(meth)acrylamidobutylsulfonic acid and 10-(meth)acrylamidodecylsulfonic acid.

(ii) Bifunctional Polymerizable Monomer

There are aromatic and aliphatic bifunctional polymerizable monomers.

Examples of the aromatic polymerizable compound include 2,2-bis((meth)acryloyloxyphenyl)propane, 2,2-bis(4-(meth)acryloyloxy-2-hydroxypropoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2,2-bis(4-(meth)acryloyloxydipropoxyphenyl)propane and 2,2-bis(4-(meth)acryloyloxyisopropoxyphenyl)propane; and urethane-based polymerizable monomers obtained by adding a (meth)acrylate compound having a hydroxyl group such as 2-hydroxyethyl(meth)acrylate, 2-hydroxyethylpropyl(meth)acrylate or 3-chloro-2-hydroxypropyl(meth)acrylate and a diisocyanate compound such as methylbenzene diisocyanate or 4,4-diphenylmethane diisocyanate.

Examples of the aliphatic compound include ethylene glycol-based or propylene glycol-based di(meth)acrylates such as ethylene glycol di(meth)acrylate, diethylene glycol di(meth)acrylate, triethylene glycol di(meth)acrylate, tetraethylene glycol di(meth)acrylate, pentamethylene glycol di(meth)acrylate, hexaethylene glycol di(meth)acrylate, nonaethylene glycol di(meth)acrylate, propylene glycol di(meth)acrylate, dipropylene glycol di(meth)acrylate, tripropylene glycol di(meth)acrylate, tetrapropylene glycol di(meth)acrylate, pentapropylene glycol di(meth)acrylate, hexapropylene glycol di(meth)acrylate and nonapropylene glycol di(meth)acrylate; di(meth)acrylate compounds having a cyclic, linear or branched aliphatic group and ethylene glycol or propylene glycol bonded together, such as ethoxylated cyclohexane di(meth)acrylate; aliphatic di(meth)acrylate compounds such as neopentyl glycol di(meth)acrylate, tricyclodecanedimethanol di(meth)acrylate, 1,4-butanediol di(meth)acrylate, 1,6-hexanediol di(meth)acrylate, 1,9-nonanediol di(meth)acrylate, 1,12-dodecanediol di(meth)acrylate and 2-hydroxy-1,3-dimethacryloxypropane; and urethane-based polymerizable monomers obtained by adding a (meth)acrylate compound having a hydroxyl group such as 2-hydroxyethyl(meth)acrylate, 2-hydroxyethylpropyl(meth)acrylate, 2-hydroxyethyl(meth)acrylate, 2-hydroxyethylpropyl(meth)acrylate, 3-chloro-2-hydroxypropyl(meth)acrylate or 2-hydroxy-1,3-dimethacryloxypropane and a diisocyanate compound such as hexamethylene diisocyanate, trimethylhexamethylene diisocyanate, methylcyclohexane diisocyanate, isophorone diisocyanate or methylenebis(4-cyclohexylisocyanate).

(iii) Trifunctional Polymerizable Monomer

Examples of the trifunctional polymerizable monomer include trimethylolpropane tri(meth)acrylate, pentaerythritol tri(meth)acrylate, dipentaerythritol tri(meth)acrylate and tris(2-(meth)acryloxyethyl)isocyanurate.

(iv) Tetra or More-Functional Polymerizable Monomer

Examples of the tetra or more-functional polymerizable monomer include tetra(meth)acrylate compounds such as pentaerythritol tetra(meth)acrylate and dipentaerythritol tetra(meth)acrylate; urethane-based polymerizable monomers obtained by adding a diisocyanate compound having an aliphatic group between diisocyanates such as hexamethylene diisocyanate, trimethylhexamethylene diisocyanate, methylcyclohexane diisocyanate, isophorone diisocyanate or methylenebis(4-cyclohexylisocyanate), a diisocyanate compound having an aromatic group such as methylbenzene diisocyanate or 4,4-diphenylmethane diisocyanate and a bi or more-functional (meth)acrylate compound having a hydroxyl group; and dipentaerythritol penta(meth)acrylate and dipentaerythritol hexa(meth)acrylate. Polyethylenically unsaturated carbamoyl isocyanurate-based compounds disclosed by JP-B 7-80736 may also be used.

When methyl(meth)acrylate, ethyl(meth)acrylate or butyl(meth)acrylate having a boiling point at normal pressure of 150° C. or lower, preferably 120° C. or lower out of the above compounds is used as the main component of the polymerizable monomer (a), an unreacted polymerizable monomer is vaporized by polymerization heat at the time of polymerization curing, thereby forming no unpolymerized layer advantageously.

To accelerate the polymerization rate and improve the abrasion resistance of the cured product and the aesthetics of the cured product by suppressing color heterogeneity, a monofunctional polymerizable monomer and a bi- or more-functional polymerizable monomer can be mixed together before use. The ratio of these monomers may be suitably selected according to the polymerization performances of the polymerizable monomers and the formation state of an unpolymerized layer. However, the ratio of the monofunctional polymerizable monomer to the bi- or more-functional polymerizable monomer is 99.5-60/0.5-40 wt %, preferably 98-65/2-35 wt %, more preferably 95-70/5-30 wt %. When the content of the polyfunctional polymerizable monomer is lower than 0.5 wt %, the improvement of abrasion resistance, the acceleration of the polymerization rate and the suppression of color heterogeneity cannot be expected and when the content of the polyfunctional polymerizable monomer is higher than 40 wt %, an unpolymerized layer is apt to remain at the time of curing, whereby it must be wiped off with a tissue containing a solvent such as acetone, thereby making operation cumbersome disadvantageously.

Compounds preferred as the monofunctional polymerizable monomer include (meth)acrylate-based polymerizable monomers such as 2-hydroxyethyl(meth)acrylate, 2-hydroxy-3-phenoxypropyl(meth)acrylate, glycidyl(meth)acrylate, methoxyethylene glycol(meth)acrylate, 3-chloro-2-hydroxypropyl(meth)acrylate, isobornyl(meth)acrylate, trifluoroethyl(meth)acrylate and perfluorooctyl(meth)acrylate besides methyl(meth)acrylate, ethyl(meth)acrylate and butyl(meth)acrylate; phosphoric acid group-containing polymerizable monomers such as 2-(meth)acryloyloxyethyl dihydrogen phosphate, 10-(meth)acryloyloxydecyl dihydrogen phosphate and 12-(meth)acryloyloxydodecyl dihydrogen phosphate; pyrophosphoric acid group-containing polymerizable monomers such as di[2-(meth)acryloyloxyethyl]pyrophosphate, di[4-(meth)acryloyloxybutyl]pyrophosphate, di[8-(meth)acryloyloxyoctyl]pyrophosphate and di[12-(meth)acryloyloxydodecyl]pyrophosphate; thiophosphoric acid group-containing polymerizable monomers such as 2-(meth)acryloyloxyethyl dihydrogen thiophosphate and 10-(meth)acryloyloxydecyl dihydrogen thiophosphate; carboxylic acid group-containing polymerizable monomers such as (meth)acrylic acid, 4-(meth)acryloyloxyethyloxycarbonyl phthalic acid, 4-(meth)acryloyloxybutyloxycarbonyl phthalic acid, 4-(meth)acryloyloxyoctyloxycarbonyl phthalic acid, 4-(meth)acryloyloxydecyloxycarbonyl phthalic acid and acid anhydrides thereof; and sulfonic acid group-containing polymerizable monomers such as 2-(meth)acrylamidoethylsulfonic acid, 3-(meth)acrylamidopropylsulfonic acid and 4-(meth)acrylamidobutylsulfonic acid.

Compounds preferred as the polyfunctional polymerizable monomer include 2,2-bis(4-(meth)acryloxyethoxyphenyl)propane and 2,2-bis(4-(meth)acryloxypolyethoxyphenyl)propane; urethane-based polymerizable monomers obtained by adding a (meth)acrylate compound having a hydroxyl group such as 2-hydroxyethyl(meth)acrylate, 2-hydroxyethylpropyl(meth)acrylate or 3-chloro-2-hydroxypropyl(meth)acrylate and a diisocyanate compound such as hexamethylene diisocyanate, methylbenzene diisocyanate or 4,4-diphenylmethane diisocyanate; and ethylene glycol di(meth)acrylate, diethylene glycol di(meth)acrylate, triethylene glycol di(meth)acrylate, neopentyl glycol di(meth)acrylate, tricyclodecanedimethanol di(meth)acrylate, 1,4-butanediol di(meth)acrylate, 1,6-hexanediol di(meth)acrylate, 2-hydroxy-1,3-dimethacryloxypropane, 1,9-nonanediol di(meth)acrylate, trimethylolpropane tri(meth)acrylate, tris(2-(meth)acryloxyethyl)isocyanurate and pentaerythritol tetra(meth)acrylate. Out of these, ethylene glycol di(meth)acrylate, diethylene glycol di(meth)acrylate, neopentyl glycol di(meth)acrylate, tricyclodecanedimethanol di(meth)acrylate, 1,4-butanediol di(meth)acrylate, 1,6-hexanediol di(meth)acrylate, 1,9-nonanediol di(meth)acrylate, trimethylolpropane tri(meth)acrylate, tris(2-(meth)acryloxyethyl)isocyanurate and pentaerythritol tetra(meth)acrylate are preferably used because a cured product having high water resistance is obtained.

A description is subsequently given of a reducing agent (c) capable of decomposing the radical generator (b). The reducing agent (c) is added to the composition I before use in the case of a two-composition type dental polymerizable composition. Any organic compound and any inorganic compound may be used as the component (c). An organic compound is preferably used because it suppresses the water absorption of the cured product and improves the coloring resistance of the cured product. As for the type of the organic compound, aromatic amines which decompose the radical generator (b) to be described hereinafter efficiently are preferred, and aromatic cyclic tertiary amines having a nitrogen atom directly bonded to an aromatic ring, such as N-di (β-hydroxyethyl)-p-toluidine, N,N-dimethyl-p-toluidine, N,N-dimethylaniline, N,N-diethyl-p-toluidine, N,N-diethylaniline, N,N-di(hydroxypropyl)-p-toluidine, N,N-di(β-hydroxyethyl)-p-toluidine, N,N-dimethyl-p-toluidine, N,N-dimethylaniline, N,N-diethylaniline and N,N-di(hydroxypropyl)-p-toluidine; aliphatic tertiary amines having a polymerizable group such as N,N-dimethylaminoethyl(meth)acrylate; and secondary amines such as N,N-diphenylglycine, N-phenylglycine and alkali metal salts of N-phenylglycine, are particularly preferred. These reducing agents may be used in combination of two or more.

To improve the storage stability and suppress the yellowing at the time of polymerization of the composition I, a polymerization inhibitor is preferably added to the composition I. The polymerization inhibitor is not limited to a particular type if it has the effect of improving the storage stability and suppressing the discoloration at the time of polymerization curing of the composition I and the discoloration of the cured product in the oral cavity. Hindered phenol-based polymerization inhibitors (j) such as 2,6-dimethyl-6-tert-butylphenol, 2,2'-methylenebis(6-tert-butyl-4-methylphenol), 1,3,5-trimethyl-2,4,6-tris(3,5-di-t-butyl-4-hydroxy benzoyl)benzene or 2,5-di-tert-butylhydroquinone can be preferably used to obtain the above effect. An ultraviolet absorbent may be added to suppress the discoloration at the time of storage of the composition I and the discoloration of the cured product. The ultraviolet absorbent is not limited to a particular type if it is a compound capable of improving the light resistance of the composition I. Benzophenone-based ultraviolet absorbents (h) which suppress the discoloration of the composition I and the discoloration of the cured product at the same time, such as 2,4-dihydroxybenzophenone, 2-hydroxy-4-methoxybenzophenone and 4-benzoyl-2-hydroxybenzophone, are preferred. The amounts of the components (j) and (k) will be specified hereinafter.

A description is subsequently given of the (meth)acrylate polymer particles (def).

The above (meth)acrylate polymer particles (def) comprise powders (d) having a particle size distribution of 65 to 400 μm, a median diameter of 70 to 120 μm and a molecular weight ($M_G$) in terms of PMMA measured by GPC of 500,000 to 1,150,000, powders (e) having a particle size distribution of 65 to 400 μm, a median diameter of 70 to 120 μm and a molecular weight ($M_G$) in terms of PMMA measured by GPC of more than 1,150,000 and 2,000,000 or less, and powders (f) having a particle size distribution of 10 to 65 μm, a median diameter of 20 to 60 μm and a molecular weight ($M_G$) in terms of PMMA measured by GPC of 300,000 to 3,000,000 as the main components. They are preferably contained in the composition II or III though not limited to these. A description is subsequently given of each of these components (d, e and f) of the (meth)acrylate polymer particles. Known compounds may be used as the (meth)acrylate polymer. Stated more specifically, homopolymers and copolymers produced by suspension polymerizing or emulsion polymerizing the above (meth)acrylate-based polymerizable monomers or mixtures thereof may be used as the polymer powders. Preferred examples of the polymer include a methyl (meth)acrylate polymer, an ethyl(meth)acrylate polymer, a butyl(meth)acrylate polymer, a propyl(meth)acrylate polymer, a copolymer of methyl(meth)acrylate and ethyl(meth)acrylate, a copolymer of methyl(meth)acrylate and butyl (meth)acrylate, a copolymer of methyl(meth)acrylate and propyl(meth)acrylate and a copolymer of methyl(meth)acrylate and styrene. Out of these, a methyl(meth)acrylate polymer, an ethyl(meth)acrylate polymer and a copolymer of methyl(meth)acrylate and ethyl(meth)acrylate are particularly preferred because a cured product having excellent mechanical properties can be produced. Fluorine-containing (meth)acrylate polymers such as a trifluoroethyl(meth)acrylate polymer, a perfluorooctyl(meth)acrylate polymer, a copolymer of methyl(meth)acrylate and trifluoroethyl(meth)acrylate and a copolymer of ethyl(meth)acrylate and trifluoroethyl(meth)acrylate may also be used to improve contamination resistance if they have high miscibility with the composition I and can obtain performance such as the handling property of the present invention.

Crosslinkable polymer powders (j) such as powders of a copolymer of a monofunctional polymerizable monomer and a polyfunctional polymerizable monomer, for example, crosslinkable polymer powders of methyl(meth)acrylate and trimethylolpropane tri(meth)acrylate, or crosslinkable polymer powders of trimethylolpropane tri(meth)acrylate may be added to the composition II or III in limits that ensure that the abrasion resistance, mechanical properties and coloring resistance of the cured product are improved and the handling property and curability of the dental polymerizable composition of the present invention are not impaired. The content of the crosslinkable polymer powders is preferably 1 to 50 wt %, more preferably 1 to 30 wt %, much more preferably 3 to 20 wt % based on the total of the above powders (d, e and f). When the content of the powders is lower than 1 wt %, the improvement of the abrasion resistance of the cured product may not be expected disadvantageously. When the content of the powders is higher than 50 wt %, the miscibility of the polymer powders with the composition I degrades, thereby making it difficult to build up the composition. Also, the composition I hardly infiltrates into the crosslinked part of the polymer, whereby a matrix part formed from the composition I of the cured product and a crosslinked part of the cured product are separated from each other, thereby reducing abrasion resistance and mechanical properties disadvantageously. When a crosslinked material is used, the particle size distribution and the median diameter of the crosslinked material should fall within the above ranges but the molecular weight thereof is hardly measured by a measuring method which will be described hereinafter and therefore cannot be specified because it does not dissolve in a solvent. Therefore, the degree of swelling of powders of the crosslinked material is measured in advance and can be used as an index of its molecular weight.

The particle size characteristics of the (meth)acrylate polymer powders are not particularly limited if the characteristic feature of the present invention is obtained. A description is first given of the (meth)acrylate polymer powders (d and e). The particle size distribution, the median diameter and the mode diameter given herein are values obtained by using the SALD-2000A laser diffraction particle size distribution measuring instrument of Shimadzu Corporation and ethanol as a dispersion aid at a measurement range of 0.03 to 700 μm. Since the (meth)acrylate polymer may dissolve or swell if it is measured for a long time by using ethanol as a dispersion aid, it must be measured within a time during which these phenomena do not appear. Then, to suppress changes in particle size characteristics by swelling, water may be used as a dispersion aid. When water is used, a dispersant such as sodium metaphosphate may be used to improve the dispersibility of the polymer powders. The measurement conditions are the same as those for the (meth)acrylate polymer powders (f) which will be described hereinafter.

The above powders (d and e) have a particle size distribution of 65 to 400 μm, preferably 70 to 370 μm, more preferably 75 to 350 μm and a median diameter of 70 to 120 μm. The molecular weight ($M_G$) in terms of PMMA measured by GPC of the powders (d) is 500,000 to 1,150,000, preferably 700,000 to 1,100,000, more preferably 850,000 to 1,050,000. The molecular weight ($M_G$) in terms of PMMA measured by GPC of the powders (e) is more than 1,150,000 and 2,000,000 or less, preferably 1,250,000 to 1,800,000, more preferably 1,350,000 to 1,600,000. The particle size distribution width of the above powders (f) is 10 to 65 μm, preferably 15 to 60 μm, more preferably 20 to 55 μm.

The molecular weight ($M_G$) in terms of PMMA measured by GPC is a molecular weight measured by gel permeation chromatography (GPC) and calibrated with polymethyl methacrylate (PMMA). Taking the powders (d) as an example, the converted molecular weight values (to be simply referred to as "molecular weight" hereinafter) of the powders (e) being distributed at 500,000 to 1,150,000 means that molecules having a molecular weight within the above range are existent. The powders (d) and (e) are preferably used as a mixture having a top peak or a main peak within the above molecular weight ranges or a mixture having a main weight ratio within the above ranges in the GPC measurement. For example, the highest peak (to be referred to as "first peak" hereinafter, this shall apply hereinafter) should belong to the molecular weight range of the powders (d) and the second peak should belong to the molecular weight range of the powders (e), or the integral values of the GPC measurement results are integrated for the molecular weight ranges of the powders (d) and the powders (e) and other molecular weight ranges in place of the count number of peaks, and the largest integral value should fall within the molecular weight range of the powders (d), and the second largest integral value should fall within the molecular weight range of the powders (e).

A description is subsequently given of the median diameter. The median diameters of the above powders (d) and (e) are 70 to 120 μm, preferably 73 to 110 μm, more preferably 77 to 100 μm. The median diameter of the above component (f) is 20 to 60 μm, preferably 22 to 55 μm, more preferably 25 to 50 μm. The difference between the median diameter and the average particle diameter of the powders (d) and (e) is not more than 10 μm, preferably not more than 5 μm, more preferably not more than 3 μm. The difference between the median diameter and the average particle diameter of the powders (f) is not more than 12 μm, preferably not more than 7 μm, more preferably not more than 5 μm. The mode diameters of the powders (d) and (e) are preferably 73 to 100 μm, more preferably 75 to 95 μm, much more preferably 77 to 90 μm. Further, the mode diameter of the powders (f) is preferably 15 to 65 μm, more preferably 25 to 59 μm, much more preferably 25 to 53 μm. When the particle size characteristics such as the particle size distribution widths, median diameters, differences between the median diameter and the average particle diameter and the mode diameters of the powders (d), (e) and (f) fall below the lower limits, the viscosity of slurry rises during operation, thereby deteriorating handling property, especially handling property for building up with resin by the brush-dip technique disadvantageously. When the particle size characteristics exceed the upper limits, the composition II or III is hardly dissolved in or swollen with the composition I, and rough particles are produced in the slurry, thereby reducing handling property or including air bubbles disadvantageously. The median diameter, average particle diameter and mode diameter measured by using the laser diffraction particle size distribution measuring instrument can be searched from the home page of Shimadzu Corporation.

As one of the factors for obtaining excellent slurry handling property, especially excellent handling property for building up with resin by the brush-dip technique, the molecular weight is also important in addition to the above particle size characteristics. For example, even when the particle size characteristics of the powders (d), (e) and (f) fall within the above ranges, if the molecular weights of these powders are too low, the powders are easily dissolved in the composition I, whereby the viscosity of the slurry rises immediately and handling property may be deteriorated disadvantageously. If the molecular weights are too high, the above powders are hardly swollen with or dissolved in the composition I, whereby a large amount of the (meth)acrylate-based polymer particles remain in the slurry, coarse particles remain during build-up operation, or air bubbles are contained disadvantageously. Further, the mechanical properties and aesthetics of the cured product may be deteriorated by the inclusion of air bubbles disadvantageously.

A more detailed description is subsequently given of the molecular weight characteristics of the above powders (d) and (e). The molecular weights, molecular weight distributions and peak molecular weights of the powders (d) and (e) are not particularly limited if the performance of the present invention is obtained. Preferably, the number average molecular weight (Mn) of the above powders (d) is in the range of 50,000 to 250,000 and the number average molecular weight (Mn) of the above powders (e) is in the range of 300,000 to 700,000. Data obtained in terms of PMMA measured by GPC using a column (PLgel 10μ MIXED-B, Polymer Laboratories Co., Ltd.), a column temperature (normal temperature) and a movable layer (tetrahydrofuran) are preferably used for the measurement of the molecular weight and molecular weight distribution of the polymer powders. Mn of the (meth)acrylate polymer powders (d) is preferably 50,000 to 250,000, more preferably 70,000 to 200,000, much more preferably 90,000 to 180,000. $M_G$ of the powders (d) is 500,000 to 1,140,000, preferably 700,000 to 1,100,000, more preferably 850,000 to 1,050,000 as described above. The peak molecular weight (Mp) of the powders (d) is preferably 700,000 to 1,150,000, more preferably 800,000 to 1,100,000, much more preferably 900,000 to 1,050,000. Mn of the (meth)acrylate polymer powders (e) is preferably 300,000 to 700,000, more preferably 330,000 to 600,000, much more preferably 370,000 to 500,000. $M_G$ of the powders (e) is preferably more than 150,000 and 2,000,000 or less, more preferably 1,250,000 to 1,800,000, much more preferably 1,350,000 to 1,600,000 as described above. Mp of the powders (e) is preferably 1,160,000 to 1,700,000, more preferably 1,200,000 to 1,600,000, much more preferably 1,370,000 to 1,520,000.

As for the molecular weights in terms of PMMA measured by GPC and number average molecular weights of the powders (d) and (e), when the powders (d) and (e) form a mixture, average values are calculated at ranges where these components are distributed.

A description is subsequently given of the molecular weight of the above component (f). Mn of the above component (f) is preferably 50,000 to 700,000, more preferably 120,000 to 550,000, particularly preferably 270,000 to 400,000. $M_G$ is 300,000 to 3,000,000, preferably 300,000 to 2,000,000, more preferably 500,000 to 2,000,000. Mp is preferably 300,000 to 3,000,000, more preferably 700,000 to 2,000,000, much more preferably 1,500,000 to 1,800,000.

The molecular weight distributions ($M_G$/Mn) of the above powders (d), (e) and (f) are not particularly limited if the effect of the present invention is obtained. $M_G$/Mn of the above powders (d) is preferably 4.4 to 12, more preferably 5 to 10, particularly preferably 6 to 7.5. $M_G$/Mn of the above powders (e) is preferably 2.2 to 4.4, more preferably 2.5 to 4.2, much more preferably 2.7 to 4. $M_G$/Mn of the above component (f) is preferably 2.2 to 4.4, more preferably 2.5 to 4.2, much more preferably 2.7 to 4. As for the molecular weight distributions of these three components, at least one, preferably two, particularly preferably all of the three components should have $M_G$/Mn within the above ranges.

When the molecular weight characteristics of the powders (d), (e) and (f) exceed the upper limits, coarse particles are contained in the slurry, thereby not only reducing handling property but also containing air bubbles disadvantageously. When they fall below the lower limits, the viscosity of the slurry rises during operation, thereby reducing handling property, particularly slurry releasability from the brush by the brush-dip technique disadvantageously.

The feature of the present invention is that the powders (d), (e) and (f) having specific particle size characteristics and specific molecular weight characteristics are used in combination as described above. When only the powders (d) are used, their miscibility with the composition I becomes too high, thereby causing the fall of the slurry, which is not preferred for build-up by the brush-dip technique. When only the powders (e) are used, their miscibility with the composition I becomes low, whereby the slurry does not fall but it does not spread well, which is not preferred for build-up by the brush-dip technique. When only the powders (f) are used, the slurry becomes an unmixed-in lump of powders which is hardly built up disadvantageously. When the powders (d), (e) and (f) are used at least in combination, surprisingly, the defects of these components cancel each other to improve their miscibility with the composition I, the composition II or III is easily collected into a brush for dental technicians moistened with the composition I, and the slurry hardly falls at the time of building up, spreads well and releases from the brush easily. Further, it has been found that, since few air bubbles are contained, color and mechanical properties become better. The mixing ratio of the powders (d), (e) and (f) may be suitably determined according to the operation of the present invention but preferably 5-94/94-5/0.5-30 wt %, more preferably 20-75/75-20/1.5-25 wt %, much more preferably 30-57/57-30/3-20 wt %. (Meth)acrylate polymer particles except for the above powders (d), (e) and (f) may be contained in an amount of preferably not more than 50 wt %, more preferably not more than 30 wt %, much more preferably not more than 20 wt % based on 100 wt % of the total of the components (d), (e) and (f). When the particle size characteristics and molecular weight characteristics of the powders (d), (e) and (f) fall below the lower limits, the viscosity of the slurry quickly rises, thereby causing the deterioration of handling property for building up with resin and when these characteristics exceed the upper limits, the powders (d), (e) and (f) are not swollen with or dissolved in the composition I, whereby the slurry does not spread well and easily contains air bubbles, thereby deteriorating handling property for building up with resin disadvantageously. The mixed state of the powders (d), (e) and (f) is not particularly limited, for example
(1) the powders (d), (e) and (f) are contained indifferent compositions, respectively;
(2) the powders (d), (e) and (f) are mixed together to form one composition; and
(3) an intermediate state between (1) and (2) (one is separate and the other two are mixed together).

To improve the polishability and abrasion resistance of the cured product, inorganic oxide particles (g) and composite particles (h) of a polymer and an inorganic oxide may be added to the composition II or III independently or simultaneously. The components (g) and (h) may be a mixture of two or more different types of particles. The types and shapes of the components (g) and (h) are not limited. As for the type of the inorganic oxide particles (g), any known inorganic oxide particles may be used. The inorganic oxide particles are selected from oxides, hydroxides, chlorides, sulfates, sulfites, carbonates, phosphates and silicates containing the group I, II, III or IV atom of the periodic table or a transition metal atom, and mixtures and composite salts thereof. Specific examples of the inorganic oxide particles include glass powders such as silicon dioxide, strontium glass, lanthanum glass, barium glass and borosilicate glass, quartz powders, aluminum oxide powders, titanium oxide powders, barium fluoride powders, zirconium oxide powders, tin oxide powers and other ceramic powders, and fibrous compounds such as glass fibers and metal whiskers may also be used as required. Although the inorganic oxide powders may be directly added to the composition II or III, they are preferably hydrophobilized to produce a cured product having high mechanical properties and abrasion resistance. Known surface treating agents may be used, as exemplified by silane coupling agents such as γ-(meth)acryloxypropyltrimethoxysilane, vinyl triethoxysilane, 3-aminopropylethoxysilane, 3-chloropropyltrimethoxysilane silyl isocyanate, vinyl trichlorosilane, dimethyldichlorosilane, dioctyldichlorosilane and hexamethylenedisilazane, zirconium coupling agents, titanium coupling agents and silicone-based coupling agents. To surface treat the inorganic oxide powders, (A) the inorganic oxide powders and the surface treating agent are directly mixed together by means of a ball mill, twin-cylinder mixer or Henschel mixer (dry process), (B) the inorganic oxide powders are mixed with a solvent (B1) prepared by uniformly mixing together the surface treating agent, an organic solvent such as ethanol and water, heated at 50 to 150° C. for several minutes to several hours and dried by heating or at normal temperature (wet process), or (C) the surface treating agent or the above (B1) is directly sprayed over high-temperature inorganic oxide powders (spray process). As a matter of course, a commercially available product which has already been surface treated may be used as it is, or may be further surface treated by any one of the above processes. As for the amount of the surface treating agent based on the inorganic oxide powders, the optimum value may be determined from the specific surface area of each of the inorganic oxide powders. The amount is generally 0.1 to 20 wt %, preferably 0.1 to 15 wt %, more preferably 0.1 to 10 wt % based on the total amount of the inorganic oxide powders. The particle size distribution of the inorganic oxide powders is not particularly limited if the characteristic properties of the present invention are obtained. However, it is preferably 1 to 100 μm, more preferably 1 to 50 μm, much more preferably 1 to 30 μm. The median diameter of the inorganic oxide powders is preferably 1 to 40 μm, more preferably 1 to 10 μm, much more preferably 1 to 5 μm. When the particle size distribution and the median diameter fall below the lower limits, the improvement of the mechanical properties and abrasion resistance of the cured product is not expected disadvantageously. When they exceed the upper limits, a lustered surface is not obtained at the time of polishing and also the above (meth)acrylate polymer particles (d, e, f) and the inorganic oxide particles (g) contained in the composition II or III separate from each other due to the difference of specific gravity between them, whereby homogeneous powders may not be obtained disadvantageously.

A description is subsequently given of the composite particles (h) of a polymer and an inorganic oxide. First of all, the polymer is not limited to a particular type but preferably a polymer derived from the above polymerizable monomer (a) described above or an oligomer thereof. As a mater of course, the polymer may be a homopolymer or a copolymer derived from two or more polymerizable monomers. To improve the mechanical properties of the composite and the mechanical properties of the cured product of the dental polymerizable composition of the present invention, a polymer derived from a polymerizable monomer containing a polyfunctional polymerizable monomer having 2 or more polymerizable groups or an oligomer thereof is preferred. Further, when a polymer derived from a polymerizable monomer containing a polyfunctional polymerizable monomer having 3 or more polymerizable groups is used, a double bond having reactivity remains on the surface of the composite and copolymerizes with the polymerizable monomer (a) contained in the composition I at the time of curing with the result that the drop-off of the composite particles is suppressed, thereby obtaining a cured product having excellent mechanical properties such as abrasion resistance for a long time advantageously. The content of the polymer derived from a polyfunctional polymerizable monomer having 3 or more polymerizable groups in the polymer is not particularly limited if the performance of the present invention is obtained. However, the content of the above polymer is preferably not less than 20 wt %, more preferably not less than 50 wt %, much more preferably not less than 60 wt % based on the total of all the polymers (including the polymer derived from a polyfunctional polymerizable monomer having 3 or more polymerizable groups) constituting the composite. When the content of the polymer is lower than 20 wt % based on the total of all the polymers constituting the composite, the amount of the double bond having reactivity on the surface of the composite becomes small, whereby it is hardly copolymerized with the polymerizable monomer (a) contained in the composition I at the time of polymerization, thereby causing the drop-off of the composite particles and the deterioration of mechanical properties such as abrasion resistance disadvantageously.

A preferred compound as the polymerizable monomer having 3 or more polymerizable groups is trimethylolpropane tri(meth)acrylate or dimethylolpropane tetra(meth)acrylate, and a polymerizable monomer to be used in combination with the above polymerizable monomer is preferably an urethane-based polymerizable monomer such as di((meth)acryloxyethyl)trimethylhexamethylene diurethane or a (meth)acrylate-based polymerizable monomer having an aromatic ring and an ether bond such as 2,2-bis(4-(meth)acryloxypolyethoxyphenyl)propane. To produce the composite under heating, when a polymerizable monomer having a hetero atom of an aromatic ring, ether bond or urethane bond is used in an amount of preferably not more than 50 wt %, more preferably not more than 40 wt %, much more preferably not more than 30 wt % based on the total of all the polymerizable monomers, yellowing hardly occurs at the time of producing the composite by heat polymerization or a heat treatment which will be described hereinafter, thereby making it possible to produce composite powders which are rarely colored. As for the combination and weight ratio of preferred polymerizable monomers, a combination of trimethylolpropane tri(meth)acrylate and/or dimethylolpropane tetra(meth)acrylate and di((meth)acryloxyethyl)trimethylhexamethylene diurethane and/or 2,2-bis(4-(meth)acryloxypolyethoxyphenyl)propane is preferred, and trimethylolpropane tri(meth)acrylate and/or dimethylolpropane tetra(meth)acrylate are/is contained in a total amount of preferably 40 to 99 wt %, more preferably 50 to 95 wt %, much more preferably 50 to 90 wt %.

The inorganic oxide used in the composite is not particularly limited, and the above-described inorganic oxide particles (g) or inorganic oxide fine particles (g1) having an average primary particle diameter of 0.001 to 1 μm such as the inorganic oxide particles of Degsa Co., Ltd. or AEROSIL of Nippon Aerosil Co., Ltd. (for example, 50, 70, 130, 200, 200V, 200CF, 200FDA, 300, 300 CF, 380, R972, R972V, R972CF, R974, RX200, RY200, R202, R805, R809, R812, NAX50, RX200, RX300, TT600, K320D, R976, R976S, OX50, TT600, MOX80, MOX170, COK84 and RM50 according to grade) may be used. As a matter of course, a mixture of two or more different types of inorganic oxide powders may be used to produce the composite. The above inorganic oxide fine powders (g1) are preferably used, and AEROSIL is more preferred as the inorganic oxide particles to be added to the composite because the polishability of the cured product containing the composite powders (h) becomes high.

The inorganic oxide powders for use in the composite may be directly used to produce the composite but the surface of each of the inorganic oxide powders is preferably surface treated by the above-described process to improve the mechanical properties of the cured product containing the composite powders. When the inorganic oxide powders (g1) which have been hydrophobilized at the time of purchase, such as AEROSIL R972 and R812, are used, they may or may not be surface treated by the above process again.

The content of the inorganic oxide powders in the composite is not particularly limited if the mechanical properties of the present invention are obtained. However, when the content is too low, the improvement of the mechanical properties of the cured product is not expected and when the content is too high, the inorganic oxide powders are not dispersed fully and uniformly into the polymerizable monomer in the step of kneading the inorganic oxide into the polymerizable monomer at the time of producing the composite, whereby the transparency and mechanical properties of the cured product containing the composite powders may deteriorate disadvantageously. Therefore, the content of the inorganic oxide powders in the composite is preferably 30 to 80 wt %, more preferably 30 to 75 wt %, much more preferably 35 to 60 wt %.

The process of producing the composite is not limited. As an example of the production process, the polymerizable monomer (a), the inorganic oxide (g) and the radical generator (b) which will be described hereinafter are mechanically mixed together by means of a mortar, roll, kneader or high-viscosity stirrer to prepare paste which is then bulk polymerized. The content of the component (b) is preferably 0.01 to 5 wt %, more preferably 0.1 to 3 wt %, much more preferably 0.1 to 1 wt % based on the polymerizable monomer. A process in which the paste is put into a template such as a metal plate, pressurized at 1 to 50 MPa with a heat compression molding machine and subjected to bulk polymerization at 80 to 200°

C., preferably 100 to 150° C. for several minutes to several hours, preferably 5 minutes to 1 hour to produce the composite may be employed. When the content of the radical generator is lower than 0.01 wt %, a large amount of an unreacted polymerizable monomer remains in the composite, thereby reducing the mechanical strength of the cured product. When the content is higher than 5 wt %, a large amount of an unreacted radical generator remains in the composite, whereby the water absorption coefficient of the cured product increases, thereby deteriorating coloring resistance disadvantageously.

As a matter of course, if the polymerizable monomer or an oligomer thereof used in the production of the composite thermally polymerizes by itself, a precursor containing no polymerization initiator may be heat polymerized as it is to produce the composite.

When the produced composite is powdery, it may be used as it is or after classification. When it is massive, it is ground to obtain powders. Although the means of grinding the massive composite is not particularly limited, preferably, a ball mill, oscillating mill, jet mill or bead mill is generally used to mechanically grind the composite, and a sift or classification apparatus is used to collect powders having a predetermined particle size. The particle size distribution and median diameter of the composite particles and advantages thereof are the same as those of the above inorganic oxide (g).

Although the composite particles may be used as a component of the composition II or III as it is, the storage stability of the composition II or III is preferably improved by deactivating a stability reducing factor such as a polymerization initiator which remains in the composite particles. Although the deactivation method is not particularly limited, the powders are heated at preferably 60 to 250° C., more preferably 80 to 150° C. for preferably several tens of minutes and several tens of hours, more preferably 5 to 20 hours because the operation is easy. The heat treatment may be carried out under normal pressure, reduced pressure or increased pressure. It is preferably carried out in an inert gas atmosphere such as nitrogen or argon, or an inert gas stream to make the yellowing of the powders difficult. To further promote the drop-off of the composite particles from the cured product, the composite particles may be surface treated with the above-described surface treating agent, treated with a solvent which can substantially dissolve the polymerizable monomer constituting the composite to dissolve and remove part or all of an unreacted monomer existent on the surface of the composite and make the surface finely uneven to provide an anchoring effect, or reacted with a polymerizable monomer having an epoxy group such as glycidyl(meth)acrylate or tetrahydrofuryl(meth)acrylate.

A description is subsequently given of the radical generator (b). Radical generators (b) are roughly divided into compounds (b-1) which decompose by itself to form a radical and compounds (b-2) which are decomposed by the above-described reducing agent (c) to form a radical. This is classification according to practical convenience and may change relatively according to use conditions and the like. The radical generator (b) is not limited to an organic compound or an inorganic compound. Since the radical generator (b-1) is often used alone, and accordingly, the polymer particles are preferably stored as the composition II separate from the radical generator, a three-composition type dental polymerizable composition is prepared. Meanwhile, since the radical generator (b-2) is relatively more stable than the radical generator (b-1) and forms a radical when it is mixed with the reducing agent (c), it can be stored together with the polymer particles without a problem and therefore a two-composition type dental polymerizable composition is prepared. However, the radical generators (b-1) and (b-2) do not limit the preparation of the composition to these.

Organic compounds are preferred from the viewpoint of the water resistance of the cured product. Out of the organic compounds, an organic peroxide is particularly preferred. Although the type of the organic peroxide is not limited, the decomposition half-life at 80° C. of the organic peroxide is preferably 10 hours or less, more preferably 7 hours or less, much more preferably 5 hours or less to improve the radical generation efficiency of redox polymerization. The lower limit value of the decomposition half-life is preferably 1 hours or more, more preferably 2 hours or more, much more preferably 3 hours or more. When the decomposition half-life falls below the lower limit, the curing time becomes too fast, whereby the composition cures during the build-up operation, thereby causing a trouble in technical operation. When the decomposition half-life exceeds the upper limit, the curing time is prolonged, thereby extending the time when a temporary prosthetic restoration is completed. When the decomposition half-life falls below the lower limit, curing becomes too fast and the slurry becomes hard during the build-up operation, thereby deteriorating handling property disadvantageously.

Preferred examples of the organic compound as (b-2) include diacyl peroxides such as acetyl peroxide, isobutyl peroxide, decanoyl peroxide, benzoyl peroxide and succinic acid peroxide; peroxy dicarbonates such as diisopropylperoxy dicarbonate, di-2-ethylhexylperoxy dicarbonate and diallylperoxy dicarbonate; peroxy esters such as tert-butylperoxy isobutyrate, tert-butyl neodecanate and cumeneperoxy neodecanate; and peroxide sulfonates such as acetylcyclohexylsulfonyl peroxide. Out of these, benzoyl peroxide is preferably used.

Examples of the inorganic compound as (b-1) include ammonium persulfate, potassium persulfate, potassium chlorate, potassium bromate and potassium perphosphate.

Examples of the organic compound as (b-1) include organic boron compounds such as triethylboron, tripropylboron, tributylboron, tri-sec-butylboron, trihexylboron and partially oxidized trialkylborons. The trialkylborons include boron compounds having linear, branched or cyclic alkyl groups with 2 to 8 carbon atoms, such as triethylboron, tripropylboron, triisopropylboron, tributylboron, tri-sec-butylbo (2)boron, triisobutylboron, tripentylboron, trihexylboron, triheptylboron, trioctylboron, tricyclopentylboron and tricyclohexylboron. As described above, the three alkyl groups may be the same, only two alkyl groups may be the same, or the three alkyl groups may be different. In this case, the alkyl groups of the above trialkyborons may be suitably used in combination.

Alkoxyalkylborons include monoalkoxydialkylborons such as butoxydibutylboron. Although alkoxyalkylborons having the alkyl moiety of the alkoxy group which is the same as the alkyl group (the raw materials are easily acquired) like the above example are preferred, the organic boron compound is not limited to these alkoxyalkylborons. The organic boron compound may be a dialkoxymonoalkylboron. Both dialkylboranes having the same two alkyl groups such as butyldicyclohexylborane and diisoamylborane and dialkylboranes having different alkyl groups may be used. Dialkylboranes in which boron atoms form a bridge between monocyclic structures or bicyclic structures such as 9-borabicyclo [3.3.1]nonane may also be used.

The partially oxidized trialkylboron include partial oxides of the above trialkylborons. Out of these, partially oxidized tributylboron is particularly preferred. The partially oxidized trialkylboron is obtained by adding preferably 0.3 to 0.9 mole, more preferably 0.4 to 0.6 mole of oxygen to 1 mole of a trialkylboron.

When tributylboron or partially oxidized tributylboron out of these organic boron compounds is used, a particularly preferred effect is obtained. The most preferred organic boron compound is partially oxidized tributylboron. As described above, the three alkyl groups may be the same, only two alkyl groups may the same, or the three alkyl groups may be different.

A polymerization initiator system comprising the radical generator (b), the reducing agent (c) and barbituric acid or a derivative thereof may be used.

The half-life of the above-described component (b) is based on data issued from NOF Corporation.

They may be used alone or in combination of two or more.

Out of these, the most preferred compounds as the radical generator (b) are benzoyl peroxide and partially oxidized tributylboron.

In the dental composition of the present invention, as long as at least the polymerizable monomer (a) and the radical generator (b) are contained in different compositions I and III, respectively, the ratio of the composition I and the composition II or III described above is not particularly limited if the characteristic properties of the present invention are obtained. However, the following composition is preferred because the storage stability of the composition is improved, the discoloration of the composition I is suppressed, and the handling property and curability of the slurry consisting of two or three compositions and the mechanical properties and abrasion resistance of the formed cured product are improved.

(i) Two-Composition Type Dental Polymerizable Composition

As for the composition of the composition I, based on 100 parts by weight of the total of all the components (the polymerizable monomer (a) and the reducing agent (c) and optionally a polymerization inhibitor (j) and an ultraviolet absorbent (k)) of the composition I, the content of the component (a) is preferably 90 to 99.5 parts by weight, more preferably 95 to 98 parts by weight, much more preferably 96 to 98 parts by weight. The content of the component (c) is preferably 0.5 to 10 parts by weight, more preferably 0.5 to 5 parts by weight, much more preferably 0.5 to 3 parts by weight. The content of the component (j) is preferably 0 to 0.5 part by weight, more preferably 0.005 to 0.3 part by weight, much more preferably 0.01 to 0.1 part by weight. The content of the component (k) is preferably 0 to 5 parts by weight, more preferably 0.05 to 2.5 parts by weight, much more preferably 0.5 to 2 parts by weight. In the composition I, if storage stability and discoloration are clinically permitted without adding the components (j) and (k), there will be no problem. However, since storage stability is improved and discoloration is suppressed by adding these components, it is preferred to add these components.

As for the composition of the composition III,
based on 100 parts by weight of the total of all the components (the (meth)acrylate polymer particles (d), (e) and (f) and the radical generator (b) and optionally the inorganic oxide particles (g) and/or the composite particles (h) of a polymer and an inorganic oxide) of the composition III, the content of the above (meth)acrylate polymer particles (d) is preferably 20 to 75 parts by weight, more preferably 25 to 70 parts by weight, much more preferably 30 to 60 parts by weight, the content of the (meth)acrylate polymer particles (e) is preferably 20 to 75 parts by weight, more preferably 25 to 70 parts by weight, much more preferably 30 to 60 parts by weight, the content of the (meth)acrylate polymer particles (f) is preferably 1 to 30 parts by weight, more preferably 1 to 25 parts by weight, much more preferably 1 to 20 parts by weight, the content of the radical generator (b) is preferably 0.05 to 10 parts by weight, more preferably 0.1 to 5 parts by weight, much more preferably 0.1 to 3 parts by weight, and the total content of the inorganic oxide particles (g) and/or the composite particles (h) of a polymer and an inorganic oxide is preferably 0 to 20 parts by weight, more preferably 1 to 15 parts by weight, much more preferably 3 to 10 parts by weight. When the inorganic oxide particles (g) and/or the composite particles (h) of a polymer and an inorganic oxide are contained at the same time, the content of the component (g) is preferably 1 to 95 parts by weight, more preferably 20 to 80 parts by weight, much more preferably 30 to 70 parts by weight based on 100 parts by weight of the total of the components (g) and (h). When the ratio of the compositions I and III is outside the above range, handling property for building up with resin may be impaired and the mechanical properties of the cured product may not be obtained disadvantageously.

(ii) Three-Composition Type Dental Polymerizable Composition

As for the composition of the composition I, based on 100 parts by weight of the total of all the components (the polymerizable monomer (a) and optionally the polymerization inhibitor (j) and the ultraviolet absorbent (k)) of the composition I, the content of the component (a) is preferably 90 to 100 parts by weight, more preferably 95 to 100 parts by weight, much more preferably 96 to 99.99 parts by weight. The content of the component (j) is preferably 0 to 0.5 part by weight, more preferably 0.005 to 0.3 part by weight, much more preferably 0.01 to 0.1 part by weight. The content of the component (k) is preferably 0 to 5 parts by weight, more preferably 0 to 2.5 parts by weight, much more preferably 0 to 2 parts by weight. In the composition I, if storage stability and discoloration are clinically permitted without adding the components (j) and (k), there will be no problem. However, since storage stability is improved and discoloration is suppressed by adding these components, it is preferred to add these components.

As for the composition of the composition II or III, based on 100 parts by weight of the total of all the components (the (meth)acrylate polymer particles (d), (e) and (f) and optionally the inorganic oxide particles (g) and/or the composite particles (h) of a polymer and an inorganic oxide) of the composition II, the content of the above (meth)acrylate polymer particles (d) is preferably 20 to 75 parts by weight, more preferably 25 to 70 parts by weight, much more preferably 30 to 60 parts by weight, the content of the (meth)acrylate polymer particles (e) is preferably 20 to 75 parts by weight, more preferably 25 to 70 parts by weight, much more preferably 30 to 60 parts by weight, the content of the (meth)acrylate polymer particles (f) is preferably 1 to 30 parts by weight, more preferably 1 to 25 parts by weight, much more preferably 1 to 20 parts by weight, and the total content of the inorganic oxide particles (g) and/or the composite particles (h) of a polymer and an inorganic oxide is preferably 0 to 20 parts by weight, more preferably 1 to 15 parts by weight, much more preferably 3 to 10 parts by weight. When the inorganic oxide particles (g) and/or the composite particles (h) of a polymer and an inorganic oxide are contained at the same time, the content of the component (g) is preferably 1 to 95 parts by weight, more preferably 20 to 80 parts by weight, much more preferably 30 to 70 parts by weight based on 100 parts by weight of the total of the components (g) and (h). When the ratio of the composition I and the composition II or III is outside the above range, handling property for building up with resin may be impaired and the mechanical properties of the cured product may not be obtained disadvantageously.

Although the composition III may be 100% composed of the radical generator (b) as a matter of course, to improve the stability of the radical generator, a stabilizer and other components (such as an aprotic solvent and an organic oligomer or an organic polymer) may be contained. For example, based on 100 parts by weight of the total of the radical generator (b), the aprotic solvent and the organic oligomer or organic polymer, the content of the radical generator (b) is preferably 40 to 100 parts by weight, more preferably 50 to 80 parts by weight, the content of the aprotic solvent is preferably 0 to 60 parts by weight, more preferably 0 to 50 parts by weight, and the content of the organic oligomer or organic polymer is preferably 0 to 40 parts by weight, more preferably 0 to 30 parts by weight.

Examples of the aprotic solvent include hydrocarbons such as pentane, hexane, cyclohexane, heptane, benzene and toluene; halogenated hydrocarbons such as fluorobenzene, dichloroethane and so-called "Freon"; ethers such as diethyl ether, diisopropyl ether, ethylene glycol dimethyl ether and tetrahydrofuran; ketones such as acetone, methyl ethyl ketone and diethyl ketone; and esters such as methyl acetate, ethyl acetate and isopropyl acetate. Out of these, alkanes, ethers, ketones and esters are preferred, and acetone, methyl ethyl ketone, ethyl acetate, hexane and diisopropyl ether are particularly preferred. These aprotic solvents may be used alone or in combination of two or more.

Preferred examples of the organic oligomer or organic polymer include liquid paraffins, liquid or solid low-molecular weight polyethylene, solid vaseline, solid wax and/or solid alkyl(meth)acrylate (co)polymers.

As for the ratio of the composition II or III to the composition I in the brush-dip technique, the amount of the composition I to be soaked up into the brush is suitably adjusted to facilitate build-up by the brush. However, the amount of the composition I to be built up each time is preferably about 0.01 to 0.1 g. The ratio of the composition II or III to the composition I in the bulk-mix technique is also suitably adjusted to achieve preferred viscosity for the production of a temporary prosthetic restoration, and the weight ratio of the composition II or III to the composition I is preferably 1:1 to 2:1.

When the composition III is used, it is added to the composition i in advance. At this point, the weight ratio of the composition I to the composition III is preferably 1:0.01 to 1:1, more preferably 1:0.02 to 1:0.5.

Further, an organic pigment, an inorganic pigment or an aggregate may be added to the composition III. To reduce color heterogeneity, at least one of the components (d), (e), (f), (g) and (h) is mechanically and/or chemically fusion bonded to and fixed to the pigment.

The composition of the present invention develops its optimum performance when its components are mixed together in the above ratio. To this end, the compositions I, II and III may be separately packed for each single dose, or a measuring spoon or measuring syringe and a brush may be attached so that a single dose of each composition can be measured accurately and easily. If they are accurately measured and mixed together, for example, the components (d), (e) and (f) may be separately contained in a plurality of compositions. When the measuring spoon or measuring syringe is used, the measurement may become inaccurate and, especially in the case of powders, it may be cumbersome to mix them together uniformly. Therefore, it is preferred to avoid such complicated separate packing.

The following examples are provided for the purpose of further illustrating the present invention but are in no way to be taken as limiting.

EXAMPLES

Raw materials used are given below.
Liquid Materials (Composition I)
MMA: methyl methacrylate
4-META: 4-methacryloxyethyloxycarbonyl phthalic anhydride
1,6HX: 1,6-hexanediol dimethacrylate
AEIN: tris(2-acryloxyethyl)isocyanurate
DMPT: N,N-dimethyl-p-toluidine
BHT: 2,6-di-tert-butyl-p-cresol
MEHQ: p-methoxyphenol
BZ: 2,4-dihydroxybenzophenone
CN: 2-(3-tert-butyl-2-hydroxy-5-methylphenyl)-5-chloro-2H-benzotriazole
Powder Materials (Composition III, Composition II in Example 9)
α: copolymer powders of methyl methacrylate and ethyl methacrylate (component d)
particle size distribution: 22 to 313 μm, median diameter: 83.8 μm, average particle diameter: 84.3 μm, mode diameter: 84.6 μm, number average molecular weight: 141,000, molecular weight in terms of PMMA measured by GPC: 951,000, molecular weight distribution: 6.8, peak molecular weight: 990,000
β: copolymer powders of methyl methacrylate and ethyl methacrylate (component e)
particle size distribution: 28 to 382 μm, median diameter: 85.1 μm, average particle diameter: 85.4 μm, mode diameter: 84.6 μm, number average molecular weight: 424,000, molecular weight in terms of PMMA measured by GPC: 1,490,000, molecular weight distribution: 3.5, peak molecular weight: 1,440,000
γ: copolymer powders of methyl methacrylate and ethyl methacrylate (component f)
particle size distribution: 28 to 65 μm, median diameter: 47.7 μm, average particle diameter: 50.0 μm, mode diameter: 46.3 μm, number average molecular weight: 348,000, molecular weight in terms of PMMA measured by GPC: 1,620,000, molecular weight distribution: 5.9, peak molecular weight: 1,560,000
ZMF: silica-zirconia filler, powder characteristic properties are described in Production Example 1
TU: composite powders of inorganic oxide powders and a polymer, powder characteristic properties are described in Production Example 2
BPO: benzoyl peroxide
Test conditions are given below.
Liquid Material 2 (Composition III)
TBBO: Super Bond Catalyst (of Sun Medical Corporation) which is a partially oxidized trialkylboron liquid obtained by adding 0.4 mole of oxygen to 1 mole of tributylboron. 0.0065 g of TBBO was mixed with 0.095 g of a monomer contained in the composition I right before use when it was applied.
Brush Applicability
(1) falling: After about 0.05 g of a slurry ball (X) collected by the brush-dip technique (prepared in a liquid (composition I)/powder (composition II) weight ratio of about 4:7 in this technique, hereinafter) was placed on a Teflon (registered trademark) plate, and about 0.05 g of a slurry ball (Y) collected again after 10 seconds was placed on X and left for 5 seconds, the degree of falling was checked based on changes in the shapes of X and Y.
○: X and Y maintain their shapes
Δ: X and Y maintain their shapes but slightly collapse
X: X and Y collapse into a mountain shape
(2) spreadability: About 0.05 g of a slurry ball (X) collected by the brush-dip technique was placed on a Teflon (registered trademark) plate, and a brush not moistened was used to spread X.
○: X is spread very smoothly by the brush without disconnection
Δ: X can be spread smoothly but not so well as ○ without disconnection
X: X spread by the brush is disconnected and cannot be spread smoothly
Air Bubbles
A glass sheet having cellophane was placed on one side of a Teflon (registered trademark) mold having a hole with a diameter of 4 mm and a thickness of 2 mm, and the Teflon mold and the glass sheet were sandwiched by clips.
The slurry was filled into the hole of the mold by the brush-dip technique, another glass sheet having cellophane was placed on the mold, and the both glass sheets were sandwiched by clips. Transmitted light was applied to the assembly to check the inclusion of air bubbles.
Small: the number of air bubbles is 5 or less
Large: the number of air bubbles is 6 or more
Bending Characteristics
Cellophane was put on a glass sheet, a Teflon (registered trademark) mold having a hole measuring 2×30×2 mm was placed on the glass sheet, and slurry prepared by the bulk-mix technique in a power/liquid weight ratio of 3:2 was poured into the hole. Cellophane and a glass sheet were placed on the mold, and the both glass sheets were sandwiched by clips. After the slurry was polymerized in a pressure polymerizer (NO-1: manufactured by Matsukaze Co., Ltd.) for 5 minutes, the sample was taken out from the mold and immersed in 37° C. water for 24 hours. A bending test was carried out by using the AGS-2000G autograph of Shimadzu Corporation at a distance between support points of 20 mm, a cross head speed of 1.0 mm/min at room temperature in accordance with a 3-point bending strength test method.
Yellowing at the Time of Polymerization Curing
A glass sheet having cellophane was placed on one side of a Teflon (registered trademark) mold having a hole with a diameter of 4 mm and a thickness of 2 mm, and the Teflon mold (registered trademark) and the glass sheet were sandwiched by clips. The slurry was filled into the hole of the mold by the brush-dip technique, another glass sheet having cellophane was placed on the mold, and the both glass sheets were sandwiched by clips. After the slurry was polymerized in a pressure polymerizer (NO-1: manufactured by Matsukaze Co., Ltd.) for 5 minutes, the sample was taken out from the mold and placed on a white plate to check the yellowing of the sample visually.
○: not yellowed
X: yellowed or browned
Discoloration of Composition I
The composition I was put into a transparent glass bottle and held against transmitted light to observe.
○: composition I is an achromatic transparent liquid
X: composition I is a chromatic transparent liquid Production Example 1

Production and Surface Treatment of Silica/Zirconia Filler: Production of ZMF

A silica/zirconia filler was produced as inorganic oxide powders by the following method. After 441 g (2.12 moles) of tetraethoxysilane (TES) and 15 g of a 1.3 wt % hydrochloric acid aqueous solution ($H_2O$/TES molar ratio=0.39, HCl/TES molar ratio=0.0025) were added to 1.50 L of isopropanol (IPA) to prepare a homogenous solution which was then left at room temperature for 2 hours (preparation of solution A1). 120 g (0.31 mole) of tetrabutoxy zirconium (TBZR) was added to 0.38 L of IPA at room temperature to prepare a homogeneous solution which was then added to the above prepared solution A1 so as to prepare a homogeneous solution (preparation of solution B1). 3.75 L of IPA and 1.5 L of 25% ammonia water were added to a separable flask and stirred at room temperature to prepare a homogeneous solution (solution C1), a solution (solution D1) prepared by dissolving 7.5 g (0.04 mole) of TES in 0.09 L of IPA was put into a dropping funnel and added dropwise to the solution C1 over 5 minutes, and then the solution B1 was put into a dropping funnel and added dropwise to the resulting solution over 5 hours. After addition, the resulting solution was kept stirred at room temperature for another 16 hours, stirring was stopped, and this solution was filtrated under reduced pressure to collect a white reaction precipitate. The white precipitate was dried at 80° C. under reduced pressure in a nitrogen atmosphere to remove the solvent so as to obtain 191 g of a dried product. This dried product was put into a 2-liter alumina pot containing 10 alumina balls having a diameter of 40 mm to be ground for 10 hours and baked at 350° C. for 3 hours and at 650° C. for 3 hours so as to obtain 152 g of a white silica/zirconia filter. 152 g of this filler was suspended in 0.30 L of ethanol, and 7.2 g of γ-methacryloxypropyltrimethoxysilane and 1.4 g of purified water were added to this suspension and refluxed for 2 hours. After the solvent was removed by an evaporator, the filler was surface treated at 80° C. for 2 hours in a nitrogen atmosphere. When the median diameter and particle size distribution of the surface treated filler were measured, the median diameter was 11.0 μm and the particle size distribution was 1 to 100 μm. This filler will be referred to as "ZMF" hereinafter.

Production Example 2

Production of Composite Powders of Inorganic Oxide Powders and a Polymer: TU 50 g of R972 (of Nippon Aerosil Co., Ltd.) was fully, mechanically kneaded into 50 g of a mixture of trimethylolpropane trimethacrylate and di(methacryloxyethyl)trimethylhexane diurethane (weight ratio of 70/30) by using Test Mixing Roll (of Yasuda Seiki Co., Ltd.) to prepare paste. After 0.3 g of benzoyl peroxide was further kneaded into this paste, the obtained product was put into a metal mold having a hole measuring 170×170×5 mm to be polymerized at 120° C. under an increased pressure of 20 MPa for 10 minutes by using a compression molding machine (YSR-10: manufactured by Shintou Metal Industry Co., Ltd.). The obtained polymer was smashed into about 1 $cm^2$ pieces by a hammer which were then put into a 1-liter magnetic pot (containing 30 magnetic balls having a diameter of 25 mm and 30 magnetic pots having a diameter of 15 mm) to be ground for 20 hours. Powders passing through a 100-mesh sieve were heated at 140° under reduced pressure for 8 hours in a nitrogen gas stream to obtain composite powders of inorganic oxide powders and a polymer (to be referred to as "TU" hereinafter). The median diameter of TU was 23.0 µm and the particle size distribution of TU was 1 to 100 µm.

Examples 1 to 9

Composition I and composition II or III were prepared and used in combination as shown in Table 1 to check handling property, discoloration and mechanical properties.

Comparative Examples 1 and 2

Composition I and composition II were prepared and used in combination as shown in Table 2 to check handling property, discoloration and mechanical properties.

Comparative Examples 3 to 11

Composition I and composition II were used in combination as shown in Table 2 to check discoloration. In Comparative Example 6, the production of a bending test sample was impossible.

TABLE 1

|  |  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| Liquid materials 1 (g) | MMA | 98.5 | 89.0 | 89.0 | 89.0 | 89.0 | 89.0 | 89.0 | 79.5 | 75.0 |
|  | 4-META | — | — | — | — | — | — | — | — | 5.0 |
|  | 1,6Hx | — | 9.5 | 9.5 | 9.5 | 9.5 | 9.5 | 9.5 | 9.5 | 10.0 |
|  | AEIN | — | — | — | — | — | — | — | 9.5 | 10.0 |
|  | DMPT | 1.5 | 1.5 | 1.5 | 1.5 | 1.5 | 1.5 | 1.5 | 1.5 | — |
|  | BHT | 0.03 | 0.03 | 0.03 | 0.03 | 0.03 | 0.03 | 0.03 | 0.03 | 0.03 |
|  | MEHQ | — | — | — | — | — | — | — | — | — |
|  | Bz | — | 0.75 | 0.75 | 0.75 | 0.75 | 0.75 | 0.75 | 0.75 | — |
|  | CN | — | — | — | — | — | — | — | — | — |
| Powder materials (g) | α | 46.75 | 46.75 | 44.25 | 44.25 | 41.75 | 40.0 | 40.0 | 38.5 | 36.0 |
|  | β | 46.75 | 46.75 | 44.25 | 44.25 | 41.75 | 40.0 | 40.0 | 45.0 | 50.0 |
|  | γ | 5.0 | 5.0 | 5.0 | 5.0 | 5.0 | 10.0 | 10.0 | 10.0 | 9.0 |
|  | TU | — | — | 5.0 | — | 5.0 | 8.5 | 4.0 | 5.0 | 5.0 |
|  | ZMF | — | — | — | 5.0 | 5.0 | — | 4.5 | — | — |
|  | BPO | 1.5 | 1.5 | 1.5 | 1.5 | 1.5 | 1.5 | 1.5 | 1.5 | — |
| Liquid material 2 (g) | TBBO | — | — | — | — | — | — | — | — | ◯ |
| Results | Brush applicability | ◯ | ◯ | ◯ | ◯ | ◯ | ◯ | ◯ | ◯ | ◯ |
|  | Spreadability | ◯ | ◯ | ◯ | ◯ | ◯ | ◯ | ◯ | ◯ | ◯ |
|  | Bending strength (MPa) | 72.0 | 75.0 | 78.0 | 79.5 | 82.3 | 80.0 | 77.5 | 86.0 | 82.0 |
|  | Maximum strain (%) | 8.0 | 7.6 | 7.2 | 6.9 | 6.4 | 6.7 | 7.0 | 7.4 | 8.0 |
|  | Discoloration of liquid material | ◯ | ◯ | ◯ | ◯ | ◯ | ◯ | ◯ | ◯ | ◯ |
|  | Discoloration of cured product | ◯ | ◯ | ◯ | ◯ | ◯ | ◯ | ◯ | ◯ | ◯ |
|  | Air bubbles | ◯ | ◯ | ◯ | ◯ | ◯ | ◯ | ◯ | ◯ | ◯ |

Ex.: Example

TABLE 2

|  |  | C. Ex. 1 | C. Ex. 2 | C. Ex. 3 | C. Ex. 4 | C. Ex. 5 | C. Ex. 6 | C. Ex. 7 | C. Ex. 8 | C. Ex. 9 | C. Ex. 10 | C. Ex. 11 |
|---|---|---|---|---|---|---|---|---|---|---|---|---|
| Liquid materials (g) | MMA | 89.0 | 89.0 | 89.0 | 98.5 | 89.0 | 89.0 | 89.0 | 89.0 | 89.0 | 89.0 | 89.0 |
|  | 1,6Hx | 9.5 | 9.5 | 9.5 | 9.5 | 9.5 | 9.5 | 9.5 | 9.5 | 9.5 | 9.5 | 9.5 |
|  | DMPT | 1.5 | 1.5 | — | 1.5 | 1.5 | 1.5 | 1.5 | 1.5 | 1.5 | 1.5 | 1.5 |
|  | BHT | — | — | 1.5 | 0.03 | 0.03 | 0.03 | 0.03 | 0.03 | 0.03 | 0.03 | 0.03 |
|  | MEHQ | 0.03 | — | — | — | — | — | — | — | — | — | — |
|  | Bz | — | — | 0.03 | 0.75 | 0.75 | 0.75 | 0.75 | 0.75 | 0.75 | 0.75 | 0.75 |
|  | CN | — | 0.75 | 0.75 | — | — | — | — | — | — | — | — |
| Powder materials (g) | α | 40.0 | 40.0 | 40.0 | 98.5 | — | — | 49.25 | 93.5 | — | 45.0 | 93.5 |
|  | β | 30.0 | 30.0 | 30.0 | — | 98.5 | — | 49.25 | — | 93.5 | 45.0 | — |
|  | γ | 15.0 | 15.0 | 15.0 | — | — | 98.5 | — | 5.0 | 5.0 | — | 5.0 |
|  | TU | 13.5 | 13.5 | 13.5 | — | — | — | — | — | — | 8.5 | — |
|  | ZMF | — | — | — | — | — | — | — | — | — | — | 8.5 |
|  | BPO | 1.5 | 1.5 | 1.5 | 1.5 | 1.5 | 1.5 | 1.5 | 1.5 | 1.5 | 1.5 | 1.5 |
| Results | Brush applicability | ◯ | ◯ | ◯ | X | ◯ | X | ◯ | X | ◯ | ◯ | X |
|  | Spreadability | ◯ | ◯ | ◯ | ◯ | X | X | △ | ◯ | X | △ | ◯ |
|  | Bending strength (MPa) | 86.0 | 85.5 | 82.4 | 85.5 | 82.0 | — | 79.5 | 82.3 | 80.0 | 70.0 | 89.0 |

TABLE 2-continued

|  | C. Ex. 1 | C. Ex. 2 | C. Ex. 3 | C. Ex. 4 | C. Ex. 5 | C. Ex. 6 | C. Ex. 7 | C. Ex. 8 | C. Ex. 9 | C. Ex. 10 | C. Ex. 11 |
|---|---|---|---|---|---|---|---|---|---|---|---|
| Maximum strain (%) | 5.8 | 5.7 | 5.1 | 8.5 | 8.0 | — | 7.5 | 7.0 | 7.4 | 7.6 | 4.9 |
| Discoloration of liquid material | X | X | X | ○ | ○ | ○ | ○ | ○ | ○ | ○ | ○ |
| Discoloration of cured product | X | X | X | ○ | ○ | ○ | ○ | ○ | ○ | ○ | ○ |
| Air bubbles | ○ | ○ | ○ | X | X | X | ○ | X | X | ○ | X |

C. Ex.: Comparative Example

EFFECT OF THE INVENTION

According to the present invention, there is provided a dental polymerizable composition which has excellent handling property by the brush-dip technique and the bulk-mix technique, particularly excellent handling property for building up with resin by the brush-dip technique (slurry hardly falls, spreads well and releases from a brush easily), contains few air bubbles, is excellent in color tone, polishability, mechanical properties and discoloration resistance and is used for many purposes such as the repair of a denture base or artificial tooth, a tooth crown prosthetic restoration and a temporary prosthetic restoration which is used until a bridge is completed when it is a two composition type self-curing resin.

The invention claimed is:

1. A dental polymerizable composition comprising a polymerizable monomer (a), a radical generator (b) and (meth)acrylate polymer particles (def), wherein
the (meth)acrylate polymer particles (def) comprise, as main components, powders (d), powders (e) and powders (f),
said powders (d) having a particle size distribution of 65 to 400 µm, a median diameter of 70 to 120 µm and a molecular weight ($M_G$) in terms of PMMA measured by GPC of 500,000 to 1,150,000,
said powders (e) having a particle size distribution of 65 to 400 µm, a median diameter of 70 to 120 µm and a molecular weight ($M_G$) in terms of PMMA measured by GPC of more than 1,150,000 and less than 2,000,000, and
said powders (f) having a particle size distribution of 10 to 65 µm, a median diameter of 20 to 60 µm and a molecular weight ($M_G$) in terms of PMMA measured by GPC of 300,000 to 3,000,000; and
at least the polymerizable monomer (a) and the radical generator (b) are contained in different compositions I and III, respectively, and a mixture of these compositions is curable.

2. The dental polymerizable composition according to claim 1, wherein the (meth)acrylate polymer particles (def) are contained in the composition III.

3. The dental polymerizable composition according to claim 1, wherein the (meth)acrylate polymer particles (def) are contained in composition II separate from the compositions I and III.

4. The dental polymerizable composition according to claim 1, wherein a reducing agent (c) capable of decomposing the radical generator (b) is contained in the composition I.

5. The dental polymerizable composition according to claim 1, wherein the molecular weight ($M_G$) in terms of PMMA measured by GPC of the powders (f) is 300,000 to 2,000,000.

6. The dental polymerizable composition according to claim 1, wherein the powders (d) have a molecular weight distribution (molecular weight ($M_G$) in terms of PMMA measured by GPC/number average molecular weight (Mn) in terms of PMMA measured by GPC) of 4.4 to 12, the powders (e) have a molecular weight distribution of 2.2 to 4.4 and/or the powders (f) have a molecular weight distribution of 2.2 to 4.4.

7. The dental polymerizable composition according to claim 1, wherein the composition III further comprises inorganic oxide particles (g) and/or composite particles (h) of a polymer and an inorganic oxide.

8. The dental polymerizable composition according to claim 1, wherein the radical generator (b) has a decomposition half-life at 80° C. of 10 hours or less.

9. The dental polymerizable composition according to claim 1, wherein the composition I further comprises a hindered phenol compound (j) as a polymerization inhibitor.

10. The dental polymerizable composition according to claim 1, wherein the composition I further comprises a benzophenone ultraviolet absorbent (k).

11. The dental polymerizable composition according to claim 1, wherein the (meth)acrylate polymer particles are a powder mixture having a particle size distribution that at least one particle diameter peak is existent at a range of more than 55 µm and 150 µm or less and also at a range of 20 to 55 µm and at least three number average molecular weight (Mn) peaks Pd, Pe and Pf at a range of 50,000 or more and less than 200,000, a range of more than 350,000 and 500,000 or less and a range of 200,000 to 350,000, respectively.

12. The dental polymerizable composition according to claim 1, wherein the content of powders having a particle diameter of 65 to 400 µm is 99 to 70 wt %, the content of powders having a particle diameter of 1 to 30 µm is 1 to 30 wt %, the content of powders having a number average molecular weight (Mn) of 50,000 up to but not including 200,000 is 20 to 75 wt %, the content of powders having a number average molecular weight (Mn) of 400,000 to 550,000 is 20 to 75 wt %, and the content of powders having a number average molecular weight (Mn) of 200,000 to 400,000 is 1 to 30 wt % based on 100 wt % of the total of the (meth)acrylate polymer particles.

13. A dental polymerizable composition kit for preparing the compositions of the dental polymerizable composition of claim 1.

14. The dental polymerizable composition according to claim 3, wherein the composition II further comprises inorganic oxide particles (g) and/or composite particles (h) of a polymer and an inorganic oxide.

15. The dental polymerizable composition according to claim 3, further comprising:
- a reducing agent (c) capable of decomposing the radical generator (b) contained in the composition I and/or the composition II,
- the composition I further comprises a hindered phenol compound (j) as a polymerization inhibitor,
- the composition I further comprises a benzophenone ultraviolet absorbent (k),
- the composition II further comprises inorganic oxide particles (g) and/or composite particles (h) of a polymer and an inorganic oxide,
- wherein the content of the component (a) is 90 to 99.5 parts by weight, the content of the component (c) is 0.5 to 10 parts by weight, the content of the component (j) is 0 to 0.5 part by weight and the content of the component (k) is 0 to 5 parts by weight based on 100 parts by weight of the total of the components (a), (c), (j) and (k) of the composition I, and the content of the component (d) is 20 to 75 parts by weight, the content of the component (e) is 20 to 75 parts by weight, the content of the component (f) is 1 to 30 parts by weight, the content of the component (g) and/or the component (h) is 1 to 20 parts by weight and the content of the component (b) is 0.05 to 10 parts by weight based on 100 parts by weight of the total of the components (d), (e), (f) and (g) and/or (h) and (b) of the composition II.

16. The dental polymerizable composition according to claim 3, wherein:
- the composition I further comprises a hindered phenol compound (j) as a polymerization inhibitor,
- the composition I further comprises a benzophenone ultraviolet absorbent (k),
- the composition II further comprises inorganic oxide particles (g) and/or composite particles (h) of a polymer and an inorganic oxide,
- wherein the content of the component (a) is 90 to 99.5 parts by weight, the content of the component (j) is 0 to 0.5 part by weight and the content of the component (k) is 0 to 5 parts by weight based on 100 parts by weight of the total of the components (a), (j) and (k) of the composition I, the content of the component (d) is 20 to 75 parts by weight, the content of the component (e) is 20 to 75 parts by weight, the content of the component (f) is 1 to 30 parts by weight and the content of the component (g) and/or the component (h) is 1 to 20 parts by weight based on 100 parts by weight of the total of the components (d), (e), (g) and (g) and/or (h) of the composition II, and the composition III is composed of the component (b) alone or the component(b) diluted with an organic solvent which does not react with the component (b).

17. The dental polymerizable composition according to claim 3, wherein a reducing agent (c) capable of decomposing the radical generator (b) is contained in the composition I and/or the composition II.

18. The dental polymerizable composition according to claim 3, wherein a reducing agent (c) capable of decomposing the radical generator (b) is contained in the composition II.

19. The dental polymerizable composition according to claim 14, wherein the component (h) comprises a polymer (i) derived from a tri or more-functional polymerizable monomer.

20. The dental polymerizable composition according to claim 14, wherein the inorganic oxide particles (g) and/or the composite particles (h) of a polymer and an inorganic oxide have a particle size distribution of 1 to 100 μm and a median diameter of 1 to 40 μm.

21. The dental polymerizable composition according to claim 7, wherein the component (h) comprises a polymer (i) derived from a tri or more-functional polymerizable monomer.

22. The dental polymerizable composition according to claim 7, wherein the inorganic oxide particles (g) and/or the composite particles (h) of a polymer and an inorganic oxide have a particle size distribution of 1 to 100 μm and a median diameter of 1 to 40 μm.

* * * * *